United States Patent
Gao (10) Patent No.: US 8,427,637 B2
(45) Date of Patent: Apr. 23, 2013

(54) OPTICAL DETECTION SYSTEM

(75) Inventor: Songping Gao, Ashland, MA (US)

(73) Assignee: Analogic Corporation, Peabody, MA (US)

(*) Notice: Subject to any disclaimer, the term of this patent is extended or adjusted under 35 U.S.C. 154(b) by 212 days.

(21) Appl. No.: 13/072,857

(22) Filed: Mar. 28, 2011

(65) Prior Publication Data

US 2012/0250003 A1    Oct. 4, 2012

(51) Int. Cl.
*G01N 1/10* (2006.01)

(52) U.S. Cl.
USPC .......................................... 356/246; 356/301

(58) Field of Classification Search ............ 356/301, 356/244, 246
See application file for complete search history.

(56) References Cited

U.S. PATENT DOCUMENTS

| | | | |
|---|---|---|---|
| 7,599,060 B2* | 10/2009 | Hoshizaki et al. | 356/317 |
| 2005/0110990 A1* | 5/2005 | Koo et al. | 356/301 |
| 2009/0097022 A1* | 4/2009 | Shen et al. | 356/301 |

FOREIGN PATENT DOCUMENTS

WO    WO0118524 A2 *  3/2001

* cited by examiner

*Primary Examiner* — Layla Lauchman
(74) *Attorney, Agent, or Firm* — Driggs, Hogg, Daugherty & Del Zoppo Co., LPA (57) ABSTRACT

An optical detection system includes a detector configured to detect a signal emitted from a sample carrier and generate an output indicative of the signal detected by the detector. The sample carrier emits the signal in response to the sample carrier being scanned by an excitation source, the emitted signal is indicative of a structural characteristic of the sample carrier, and the sample carrier includes bulk material, at least one material free chamber and a bulk material/chamber interface for each chamber. The optical detection system further includes a data evaluator that identifies the structural characteristic of the sample carrier based on the output of the detector and generates data indicative of the identified structural characteristic.

24 Claims, 5 Drawing Sheets

OPTICAL DETECTION SYSTEM

TECHNICAL FIELD

The following generally relates to an optical detection system and is described with a particular application to micro-channel devices and DNA analysis. However, the following is also amenable to other applications.

BACKGROUND

A micro-channel device includes one or more micro (submillimeter) channels through which one or more small volumes of samples are routed for processing and/or analysis. An example of such a device includes a biochip, a lab-on-a-chip, and/or other micro-channel device. An application in which a micro-channel device has been used is DNA sequencing. DNA sequencing generally is a method for determining an order of nucleotide bases (adenine, guanine, cytosine, and thymine) of DNA in a sample of DNA.

For DNA sequencing, the DNA in the sample is lysed, producing fragments of sequences of the four nucleotides. The fragments are replicated through polymerase chain reaction (PCR) and labeled with target specific fluorescent dyes (e.g., one for each nucleotide base), each dye having a different spectral emission characteristic (e.g., wavelength, frequency, energy and color). The labeled fragments are separated by size through electrophoresis. The DNA fragments are sequenced based on the spectral characteristics of the dyes. This has included using an optical detection system to illuminate the fragments with an excitation signal and detecting the fluoresced radiation of the dyes. The detected spectral information is used to identify the nucleotides and sequence the DNA.

Figure 1:
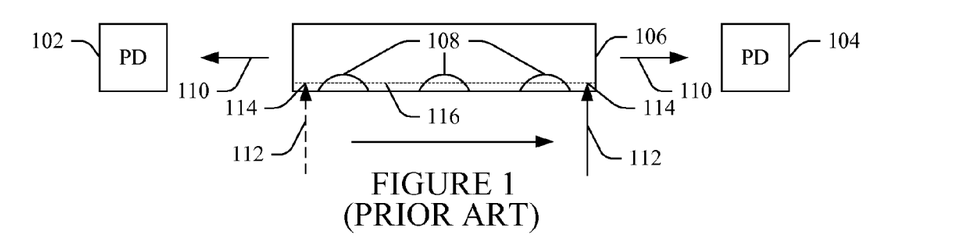
FIGS. 1-5 illustrate a prior art approach to identifying micro-channel locations in a micro-channel device.

A micro-channel location identification routine is performed on the micro-channel device before the fragment reaches the optical reading region for processing. This information is subsequently used by the optical detection system to focus the excitation signal at the fragments in the device and correlate a detected signal with the corresponding channel. One approach to identifying the location of the micro-channels has been based on a level of a detected reflected excitation signal. An example of this is shown in FIG. 1. In FIG. 1, photodiode (PD) 102 and (PD) 104 are located on opposing sides of a micro-channel device 106, which includes a plurality of micro-channels 108. The micro-channel device 106 is scanned by an excitation signal 112 with a focal spot 114 at a depth corresponding to a height of a center region 116 of the channels 108, and the photodiodes 102 and 104 detect reflected excitation signals 110.

Figure 2:
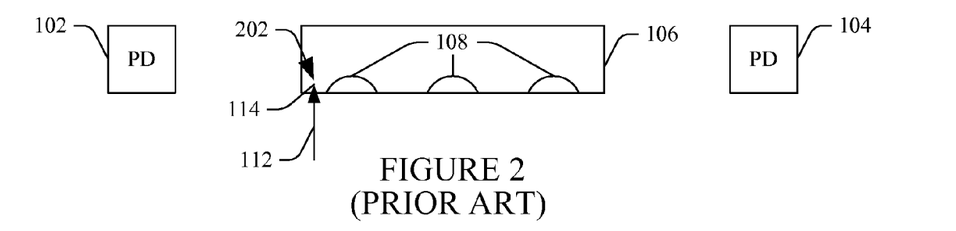
Figure 3:
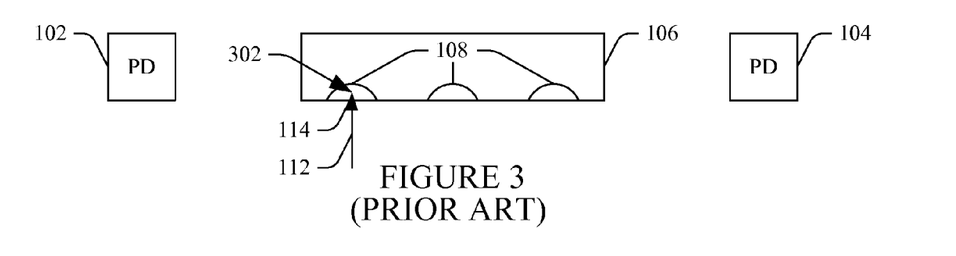

The level of the detected reflected excitation signal 110 depends on a material composition of the region of the micro-channel device 106 illuminated by the excitation signal 112. This is shown in FIGS. 2, 3, 4 and 5. In FIG. 2, the focal spot 114 of the excitation signal 112 is in a bulk material region 202 of the micro-channel device 106 where little to none of the excitation signal 112 is reflected. As a consequence, the level of any reflected signal detected by the photodiodes 102 and 104, and hence their respective outputs, is relatively small. In FIG. 3, the focal spot 114 of the excitation signal 112 is in a non-material region 302 of a micro-channel 108 of the micro-channel device 106 where little to none of the excitation signal 112 is reflected. Likewise, the level of any reflected signal detected by the photodiodes 102 and 104, and hence their respective outputs, is relatively small.

Figure 4:
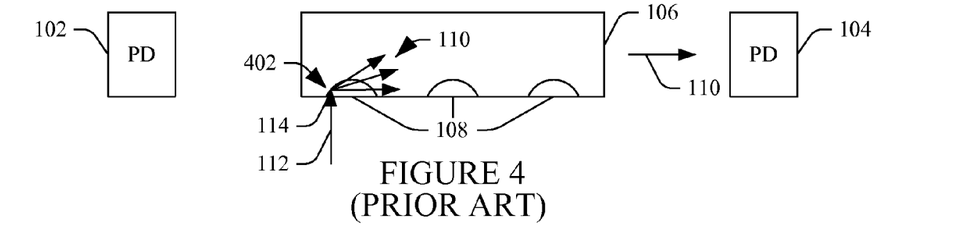
Figure 5:
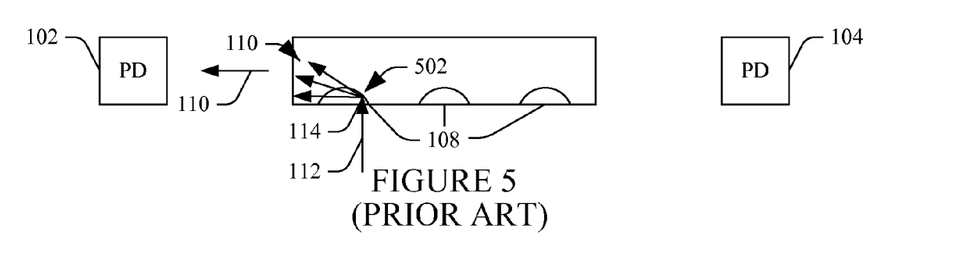

In FIG. 4, the focal spot 114 is on a bulk material region/non-material region interface 402 on the photodiode 102 side of the micro-channel 108, and a portion of the excitation signal 112 is reflected through the micro-channel 108 towards the photodiode 104, which detects the deflected excitation signal 110. In FIG. 5, the focal spot 114 is on a bulk material region/non-material region interface 502 on the photodiode 104 side of the micro-channel 108, and a portion of the excitation signal 112 is reflected through the micro-channel 108 towards the photodiode 102. In this instance, the photodiodes 102 and 104 detect the reflected excitation signal, and generate output signals having amplitudes indicative of the levels of the detected reflected signals.

From FIGS. 2-5, the level of the deflected excitation signal 110 detected by and the amplitude of the signal output by the photodiodes 102 and 104 is indicative the region of the micro-channel device 106 illuminated by the excitation signal 112. As such, with this approach, the excitation signal 112 is scanned across the micro-channel device 106, and the amplitude of the signal output by the photodiodes 102 and 104 is recorded and mapped to the scan position of the excitation signal 112 on the micro-channel device 106. The micro-channels 108 are located in the micro-channel device 106 based on the peaks or maximums in the recorded signals, which correspond to the interfaces 402 and 502, which correspond to the edges of the micro-channels 108. The locations of the micro-channels 108 are then used by the optical detection system to focus the excitation signal 112 at the samples for processing.

Unfortunately, the above approach requires additional hardware (i.e., the photodiodes 102 and 104), and this additional hardware may increase overall optical detection system cost, complexity and/or footprint. Furthermore, the optical detection system also has to additionally be configured to process the signals output by the photodiodes 102 and 104.

SUMMARY

Aspects of the application address the above matters, and others.

In one aspect, an optical detection system includes a detector configured to detect a signal emitted from a sample carrier and generate an output indicative of the signal detected by the detector. The sample carrier emits the signal in response to the sample carrier being scanned by an excitation source, the emitted signal is indicative of a structural characteristic of the sample carrier, and the sample carrier includes bulk material, at least one material free chamber and a bulk material/chamber interface for each chamber. The optical detection system further includes a data evaluator that identifies the structural characteristic of the sample carrier based on the output of the detector and generates data indicative of the identified structural characteristic.

In another aspect, a method includes obtaining a signal indicative of a structural characteristic of a sample carrier. The signal is emitted by the sample carrier in response to illuminating the sample carrier with an excitation source. The method further includes obtaining information indicative of an origin of the emission of the signal from the sample carrier. The method further includes determining a location of a chamber of the sample carrier based on the signal and the information. The method further includes employing the location to focus another excitation source at a sample in the chamber for processing the sample in the chamber.

In another aspect, computer readable instructions encoded on computer readable storage medium, which, when executed by a processor of a computing system causes the processor to: identify a location of a chamber of a sample carrier based on a signal emitted from the sample carrier and employ the location of the chamber to direct an excitation signal at a sample in the chamber to process the sample.

BRIEF DESCRIPTION OF THE DRAWINGS

The application is illustrated by way of example and not limitation in the figures of the accompanying drawings, in which like references indicate similar elements and in which.

DETAILED DESCRIPTION

Figure 6:
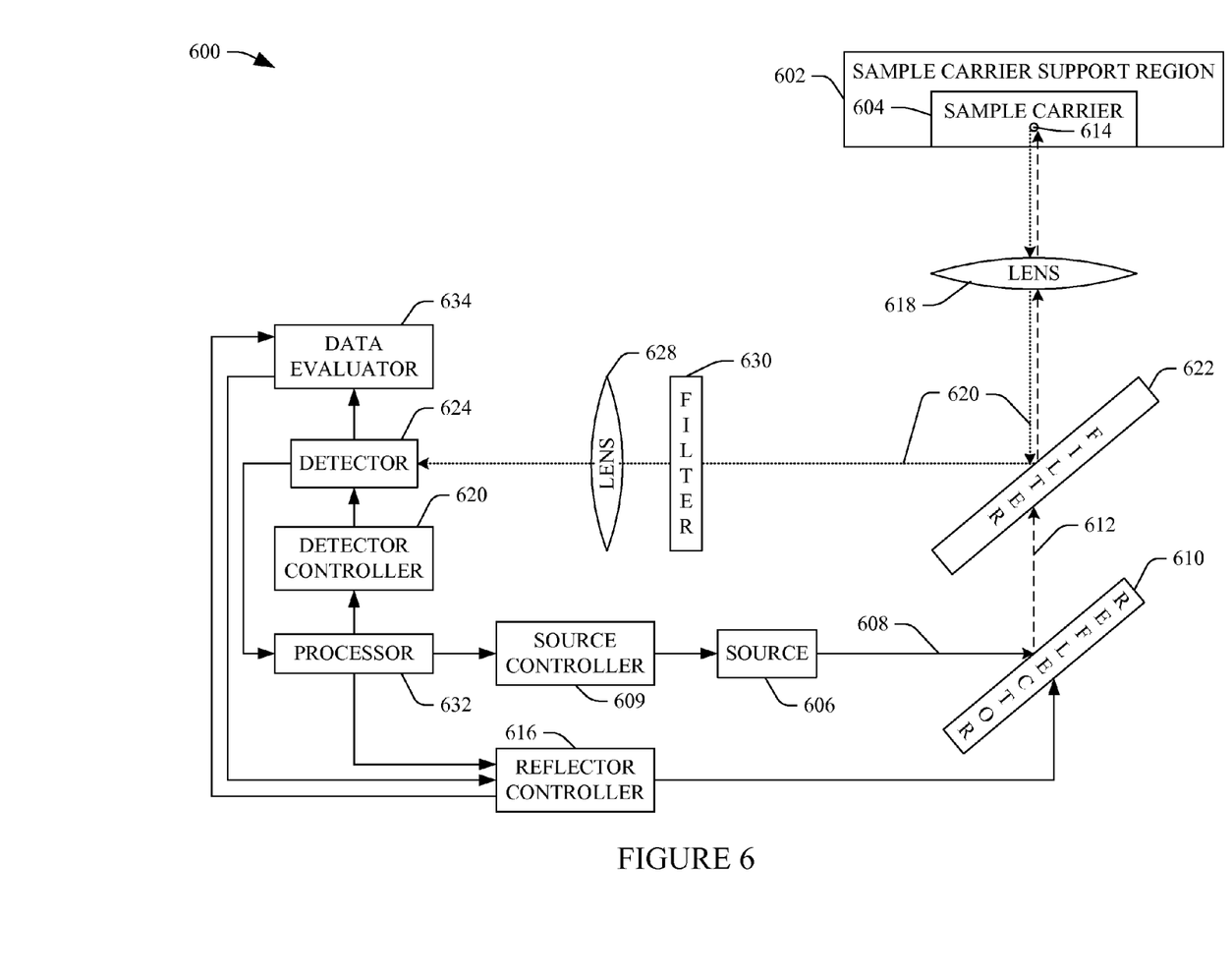
FIG. 6 illustrates an example optical detection system including data evaluator that identifies locations of micro-channels of a sample carrier.

FIG. 6 illustrates an example optical detection system 600. The optical detection system 600 may be a stand alone system or part of another system such as a sample processor and/or analyzer, including, but not limited to, a DNA sequencer and/or other apparatus. The optical detection system 600 includes a sample carrier support region 602, which is configured to receive and support a sample carrier 604 for processing sample carried thereby. Examples of a suitable sample carrier include, but are not limited to, micro-channel devices such as a lab-on-a-chip (LOC), a biochip, micro-fluidic arrays, and/or other micro-channel devices and/or sample carriers.

Figure 7:
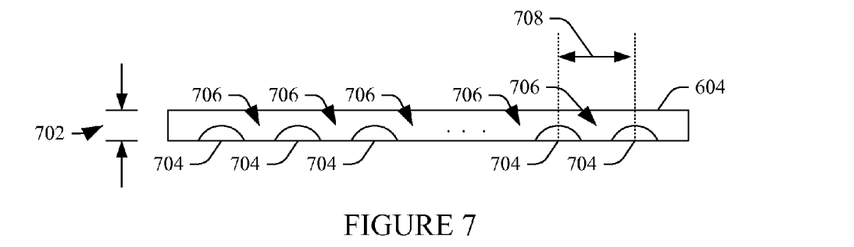
FIG. 7 illustrates an example of the sample carrier.

Turning briefly to FIG. 7, a cross sectional view along a width of an example of the sample carrier 604 is illustrated. In FIG. 7, the sample carrier 604 has a depth 702 on the order of about 180 microns, and includes one or more material-free chambers or channels 704 (e.g., 1, 16, 100, etc.) extending along the length (looking into the figure) and separated from each other by regions of bulk material 706. A center-to-center distance 708 between two neighboring channels is about 200 microns. In this example, a channel 704 is semi-circular in shape with a cross-sectional diameter. In another embodiment, the channel geometry and/or the arrangement there between may be different. The channels 704 can be used to route samples in one or more of the channels 704 and/or in other channels of the sample carrier 604.

The illustrated sample carrier 604 includes a plastic material with a refractive index of about 1.5. In one instance, the plastic material has known characteristics of emission spectrum (e.g., wavelength, intensity, peak position, etc.) for given excitation signal spectral characteristics. As described in greater detail below, the known characteristics of emission spectrum can be used, for example, in conjunction with measured emission characteristics of the sample carrier 604 to determine various properties about the sample carrier 604. A non-limiting example of such a property includes a location of a micro-channel within the sample carrier 604, a quality of a micro-channel and/or the sample carrier 604, a geometry (e.g., size and/or shape) of a micro-channel, and/or other properties.

Returning to FIG. 6, the sample carrier 604 is configured to carry one or more samples for processing. A non-limiting example of a suitable sample includes a bio-sample such as one or more labeled DNA fragment and/or other sample. A suitable label includes a fluorescent or other material that absorbs an incident excitation signal (electromagnetic radiation) and emits a corresponding characteristic signal. In the context of DNA analysis, the label may include at least four different fluorescent dyes, each dye being target specific, binding to a different one of the four nucleotide bases (adenine (A), guanine (G), cytosine (C), and thymine (T)), and emitting or fluorescing characteristic radiation. One or more other dyes may also be included. For example, a calibration dye may also be included.

An electromagnetic radiation source (source) 606 generates and transmits an excitation (source) signal 608 (electromagnetic radiation). An example of a suitable source 606 is a laser that transmits within a known electromagnetic radiation range. For DNA analysis, a narrow (e.g., 10 to 100 micron diameter) beam 488 nanometer (±5 nm) laser has been used. Other sources, including non-laser sources (e.g., a light emitting diode (LED), an incandescent light, etc.), other electromagnetic radiation wavelength ranges, and/or other diameter beams are also contemplated herein. A source controller 609 controls the source 606, including activating the source 606 transmit, adjusting the output power, pulsing transmission, etc.

A beam reflector 610 such as a mirror or other reflector directs the transmitted signal 608 along a transmission path 612 from the reflector 610 to a focal spot 614 at a depth within the sample carrier 604 corresponding to a center region of the channels 704 (FIG. 7). The reflector 610 is movably mounted, and a reflector controller 616 is configured to controllably rotate, pivot or tilt the reflector 610 to scan or move the transmission path 612 across the sample carrier 604. In one non-limiting instance, the reflector 610 is mounted on an end of a rotary shaft and the controller 616 includes an electromagnetic device such as a closed loop Galvanometer that controllably deflects the shaft to move the reflector 610 and scan the sample carrier 604.

A lens 618 is disposed between the sample carrier 604 and the reflector 610 in the transmission path 612 and is configured to focus the excitation signal 608 at the sample carrier 604. The lens 618 also focuses back scatter radiation and fluorescent radiation from the sample carrier 604 along a signal collection path 620. Note that for explanatory purposes the transmission and collection paths 612 and 620 for a particular scan location is shown, and the paths are shown spaced apart. The illustrated lens 618 includes a biconvex lens. However, other lenses such as a plano-convex or other lens that can suitably focuses the excitation signal are also contemplated herein. Moreover, the lens 618 may include more than one lens. Furthermore, in another embodiment, the lens 618 is omitted.

A filter 622 is disposed between the lens 618 and the reflector 610 in the transmission and collection paths 612 and 620. The filter 622 is configured to filter radiation traversing the transmission path 612 such that substantially only excitation electromagnetic radiation having predetermined spectral characteristics of interest passes through the filter 622. The filter 622 is also configured to filter radiation traversing the collection path 620 such that substantially only electromagnetic radiation having predetermined spectral characteristics of interest is directed along the collection path 620. An example of a suitable filter includes a dichroic filter, band-pass filter, or other filter that selectively passes electromagnetic radiation based on spectral characteristics while reflecting other electromagnetic radiation based on spectral characteristics.

A detector 624 is configured to detect electromagnetic radiation having spectral properties of interest and traversing the collection path 620 and to generate a signal indicative thereof. The detector 624 may include a photo-multiplier tube (PMT), a charge-coupled device (CCD) camera, or the like, and may be tunable or fixed. As described herein, the radiation characteristic of the sample carrier 604 and/or a sample carried by the sample carrier 604 are of interest and thus the detector 624 is configured to detect radiation having spectral properties corresponding to those of the sample carrier 604 and/or a sample carried by the sample carrier 604. In one embodiment, the detector 624 includes a plurality of sub-detectors, each configured to detect different bands of radiation within the range of interest. A detector controller 626 controls the detector 624. Such control includes, but is not limited to, adjusting the gain, activating and deactivating channels of the detector 624, etc.

A lens 628 is disposed between the filter 622 and the detector 624. The lens 628 focuses the radiation with respect to the detector 624. Similar to the lens 618, the lens 628 includes a biconvex lens, but alternatively can include other lenses such as a plano-convex or other lens that suitably focuses the radiation with respect to the detector 624. A filter 630 is disposed between the lens 628 and the filter 622. The filter 630 is configured to pass the radiation traversing the collection path and having predetermined spectral characteristics of interest and attenuate and/or reflect other electromagnetic radiation. In another embodiment, the filter 630 can be omitted. The collection path 620 is shown only for the particular scan location.

A processor 632 controls the detector controller 620, the source controller 609, and/or the reflector controller 616. The processor 632 and/or one or more processor local to the system 600, local to an apparatus including the system 600, and/or external and remote from the system may be configured to process detected signals. In the context of processing samples, this may include correlated detected signals with excitation locations on the sample carrier 604, identifying components in the sample, sequencing DNA for DNA samples, and/or other processing.

A data evaluator 634 evaluates information, including the signals generated by the detector 624. In one instance, the data evaluator 634 evaluates the signals generated by the detector 624 and determines various properties about the sample carrier 604 such as a location of a micro-channel of the sample carrier 604, a quality of a micro-channel and/or the sample carrier 604, and/or other properties. It is to be appreciated that using the data evaluator 634 may mitigate having to incorporate additional hardware such as the photodiodes 102 and 104 into the detection system relative to a configuration in which the data evaluator 634 is omitted, which may reduce overall optical detection system cost, complexity and/or footprint relative to a configuration in which the photodiodes 102 and 104 are added to the system. Furthermore, the accuracy and/or precision of the located channels may be equal to or better then that achieved using the photodiodes 102 and 104.

Optionally, the system 600, includes storage (e.g., physical memory) that can store various information such as the signals generated by the detector 624, positional information of the reflector 610 (and hence the location of the excitation signal on the sample carrier 604) and/or other information.

Figure 8:
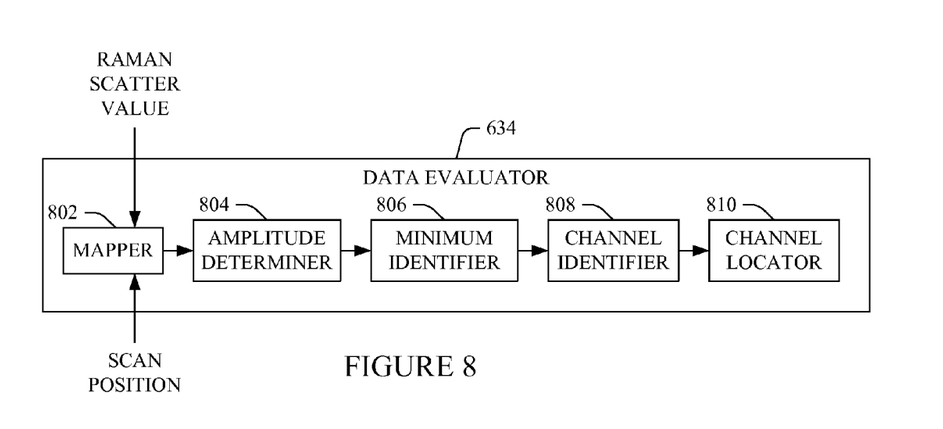
FIG. 8 illustrates an example of the data evaluator.

FIG. 8 illustrates an example of the data evaluator 634 configured to determine the location of one or more micro-channels of the sample carrier 604 based on Raman scattering.

Figure 9:
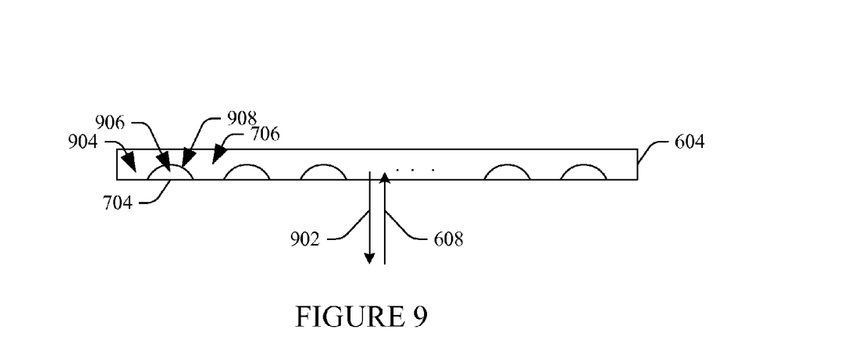
FIG. 9 illustrates an example of Raman scattering in connection with the sample carrier.

Briefly turning to FIG. 9 and with reference to FIG. 6, a portion 902 of the excitation signal 608 illuminating the sample carrier 604 inelastically scatters (via Raman scattering) back along the signal collection path 620 and has spectral characteristics (e.g., wavelength, energy, frequency and color) that correspond to the spectral characteristics of the excitation signal. For example, for the 488 nm excitation signal with a focal spot size of about 20 microns, the Raman scattering peak for the plastic material of the carrier 604 is around 570 nm±5 nm. As such, for this example, the filters 622 and 630 and the detector 624 are configured so that radiation traversing the collection path 113 having a wavelength of around 570 nm is directed towards and detected by the detector 624.

The amplitude of the Raman scattering will be greatest for bulk regions 904 of the material, lower for non-material regions 906 inside the channels 704, and lowest at the bulk material/material free interfaces 908. More particularly, for the bulk material 904, Raman scattering will be strong due to high laser power density (e.g., 200 milliwatt at 20 micron spot size).

At a non-material region 906 inside a channel 704, the laser spot is focused at non-material region, and the Raman scattering will still be generated due to the interaction between laser and material of sample carrier 604 as the laser beam passes through the material of sample carrier 604 (non focusing region). However, the intensity of Raman scattering is relatively lower than in the material 904. At the interface 908 between the bulk material 904 and the non-material region 906, the excitation signal is reflected, as described in connection with FIG. 1-5, and the amplitude of the Raman scattering will be the lowest.

Figure 10:
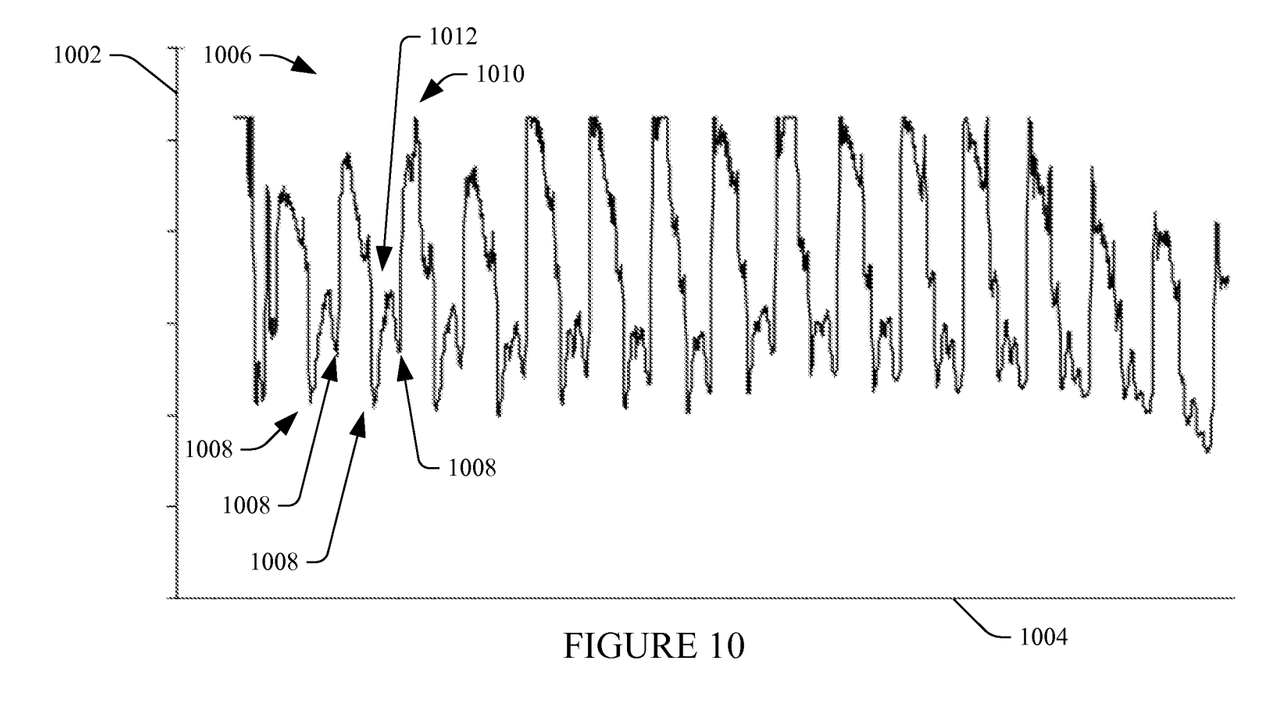
FIG. 10 graphically illustrates Raman scatter amplitude as a function of scan position along the sample carrier.

Returning to FIG. 8 and with reference also to FIG. 6, the data evaluator 634 includes a mapper 802 that maps the Raman scatter values to the scan positions on the sample carrier 604. FIG. 10 graphically shows an example of such a mapping. In FIG. 10, a y-axis 1002 represents amplitude, an x-axis 1004 represents scan position along the sample carrier 604, and the signal 1006 represents the amplitude of the detected Raman scatter signal as a function of scan position.

Returning to FIG. 8 and with further reference to FIGS. 6, 7, 9 and 10, an amplitude determiner 804 determines the amplitude of the Raman scatter value for scan positions. A minimum identifier 806 sequentially identifies local amplitude minimums 1008 (FIG. 10) along the scanned sample carrier 604. This can be achieved by comparing consecutive Raman scatter values, comparing averages of consecutive (overlapping or non-overlapping) ranges of values, etc. Thresholds corresponding to Raman peaks 1010 for the bulk material 904 and/or peaks 1012 for the non-material regions 906, an expected amplitude pattern, etc. can be used to facilitate identifying local minimums.

A channel identifier 808 identifies channels 704 based on pairs of local amplitude minimums. For example, the channel identifier 808 may identify the first two local amplitude minimums as corresponding to a first channel, a next two local amplitude minimums as corresponding to the next channel, . . . , a last two local amplitude minimums as corresponding to the last channel. A channel locater 810 locates channel 704 positions in the sample carrier 604 based on the corresponding pair of local amplitude minimums. For example, in one instance, a channel 704 is located by its center region, which is determined as a mid point region between the two positions of the pair of local amplitude minimum.

The data evaluator 634 conveys the information about the channel locations to storage (not shown), the processor 632, and/or the reflector controller 616. The reflector controller 616 can use the information to focus the source 606 at the channels 704 to illuminate samples in the channels 704 for processing the samples. The processor 632 can use the information to correlate signals detected by the detector 624 with the location of the excitation signal on the sample carrier 604, and hence the respective channels 704, for processing samples in the channels 704. The data evaluator 130 can evaluate that data dynamically in real-time as it is obtained or at later time.

Figure 11:
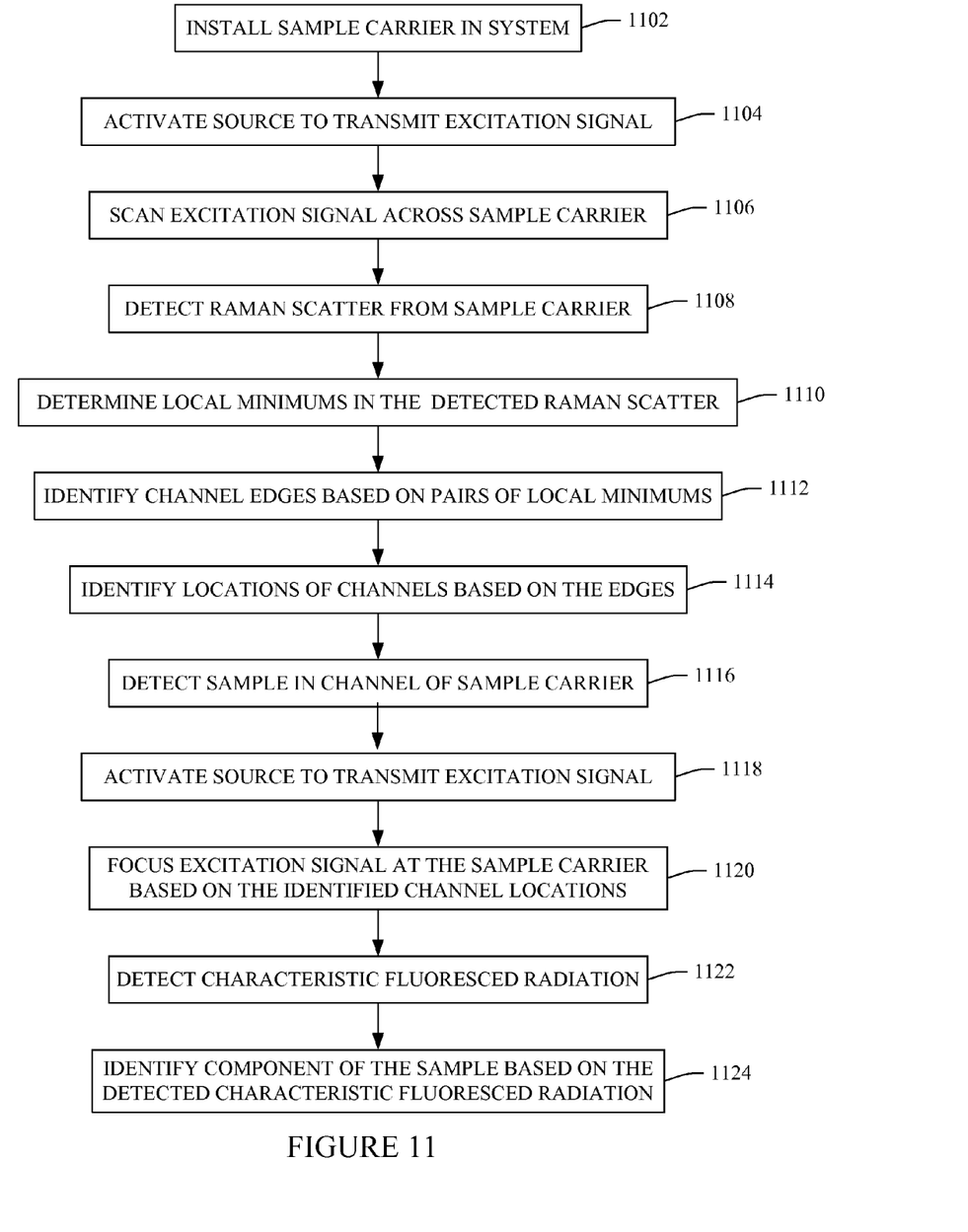
FIG. 11 illustrates a method for identifying locations of micro-channels of a sample carrier.

FIG. 11 illustrates a method that identifies locations of micro-channels of a sample carrier.

At 1102, a sample carrier is installed in connection with the optical detection system 600.

At 1104, the source 606 is activated by the source controller 609 to transmit an excitation signal 608.

At 1106, the excitation signal 608 is scanned along the sample carrier 604. This can be achieved via the reflector controller 616 controller the position and movement of the reflector 610.

At 1108, Raman scatter from the sample carrier 604 is detected by the detector 624.

At 1110, the Raman scatter, along with the corresponding location of the excitation signal on the sample carrier 604, is evaluated to determine local minimums.

At 1112, pairs of local minimums are used to identify channel edges.

At 1114, the corresponding locations of the edges are used to identify a location of a corresponding channel 704 in the sample carrier 604.

At 1116, a sample is detected to be in the channel 704.

At 1118, the source 606 is activated by the source controller 609 to transmit an excitation signal 608.

At 1120, the excitation signal 608 is focused at a channel 704 of the sample carrier 604 based on the identified locations of the channel.

At 1122, characteristic fluorescent radiation from the samples (e.g., labels therein) for a channel 704 is detected by the same detector 624.

At 1124, the characteristic fluorescent radiation is used to identify the components in the sample. In the context of DNA analysis, this may include identifying nucleotides in samples of DNA.

It is to be understood that the above acts are provided for explanatory purposes. In another embodiment, one or more acts can be added and/or one or more acts can be removed. In addition, the order of one or more of the acts can be different. Furthermore, one or more of the acts can occur concurrently.

The above acts may be implemented via one or more processors executing one or more computer readable instructions encoded or embodied on computer readable storage medium such as physical memory which causes the one or more processors to carry out the various acts and/or other functions and/or acts. Additionally or alternatively, the one or more processors can execute instructions carried by transitory medium such as a signal or carrier wave.

In another embodiment, the data evaluator 634 is configured to determine a quality of a sample carrier such as the sample carrier 604 or other micro-channel device. For this example, the sample carrier is scanned as discussed above or a predetermined sub-portion is scanned. A mapper maps the Raman scatter values to the scan positions on the sample carrier 604 as discussed herein.

A comparator compares the values at the positions with predetermined reference information in storage. In one instance, the predetermined reference includes a range of acceptable values for each position. In another instance, the predetermined reference information includes threshold values, a pattern, or the like which is compared with the values. The comparator generates a data indicative of a result of the comparison.

A quality determiner generates a signal indicative of a quality of the sample carrier based on the data. The signal is provided to the processor 632 and/or conveyed to a device external to the system 600.

The signal can be used to notify the operator of the system that the sample carrier or a portion of the sample carrier satisfied and/or did not satisfy the predetermined reference information. In one instance, a value outside of the predetermined reference information may indicate non-uniformity, a defect, a crack, etc. in the bulk material and/or at a bulk material/non-material interface of the sample carrier.

It is to be appreciated that the data evaluator 634 may be implemented via one or more processors executing one or more instructions encoded or embedded on computer readable medium such as physical memory or non-transitory medium. Additionally or alternatively, the one or more processors can also execute one or more instructions in signal medium.

The sample carrier has been described herein mainly in the context of a biochip and DNA processor for explanatory purposes. However, it is to be understood that the description herein applies to any micro-channel device for any application.

It is to be appreciated that data evaluator 634 can also process, detect and process a signal emitted by a fluid or other substance in a material free channel 704 and identify the location of the channel based on the signal.

In the embodiment described herein, the Raman scatter peak of 570 nm corresponds to the particular material of the sample carrier and the wavelength of the excitation signal. In other embodiment, in which a different material and/or a different excitation signal wavelength is employed, the Raman scatter peak may be different. Such Raman scatter peaks may be known a priori or determined.

In the example discussed herein, the channels 704 are employed to carry samples being processed. In another embodiment, the channels 704 may be used to move samples through other channels. In such an instance, a fluid such as air, a gel, water, a solution, a reagent, etc. may be move through the channels 704 and/or other channels.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. An optical detection system, comprising:
a detector configured to detect a signal emitted from a sample carrier and generate an output indicative of the signal detected by the detector,
wherein the sample carrier emits the signal in response to the sample carrier being scanned by an excitation source, the emitted signal is indicative of a structural characteristic of the sample carrier, and the sample carrier includes bulk material, at least one material free chamber and a bulk material/chamber interface for each chamber; and
a data evaluator that identifies the structural characteristic of the sample carrier based on the output of the detector and generates data indicative of the identified structural characteristic.

2. The optical detection system of claim 1, wherein the structural characteristic includes a location of a material free chamber of the sample carrier in the sample carrier.

3. The optical detection system of claim 2, wherein the structural characteristic includes an edge corresponding to a bulk material/chamber interface of the chamber, and the data evaluator determines a location of a central region of the chamber based on position information about at least two regions of the edge.

4. The optical detection system of claim 3, wherein the signal includes Raman scatter having amplitude that corresponds to the structural characteristic.

5. The optical detection system of claim 4, wherein a Raman scatter amplitude that corresponds to the edge region is a minimum.

6. The optical detection system of claim 5, wherein Raman scatter amplitudes corresponding to at least one of the bulk material or the at least one material free chamber is a maximum.

7. The optical detection system of claim 2, wherein the same detector is also configured to detect signals emitted from a sample carried in the chamber of the sample carrier, wherein the sample emits signals in response to being scanned by a sample excitation signal.

8. The optical detection system of claim 7, wherein the data indicative of the structural characteristic identifies a location of the chamber of the sample carrier, and is used to focus the sample excitation signal at the sample in the chamber.

9. The optical detection system of claim 8, wherein the sample includes at least one of a plurality of fluorescent dyes, each dye fluorescing radiation having a spectral characteristic corresponding to the respective dye and in response to being illuminated by the sample excitation signal.

10. The optical detection system of claim 9, wherein the detector is configured to detect radiation within a predetermined bandwidth range covering the spectral characteristics of the dyes, and the signal has a spectral characteristic within the predetermined bandwidth range.

11. The optical detection system of claim 9, wherein each dye is target specific and is attached to a different nucleotide in DNA fragments in the sample.

12. The optical detection system of claim 11, wherein the detector detects the signals and the detected signal are used to sequence the DNA in the sample.

13. The optical detection system of claim 1, wherein the optical detection system is part of a DNA sequencing apparatus.

14. A method, comprising:
obtaining a signal indicative of a structural characteristic of a sample carrier, wherein the signal is emitted by the sample carrier in response to illuminating the sample carrier with an excitation signal;
obtaining information indicative of an origin of the emission of the signal from the sample carrier;
determining a location of a chamber of the sample carrier based on the signal and the information; and
employing the location to focus a second excitation signal at a sample in the chamber for processing the sample in the chamber.

15. The method of claim 14, wherein the structural characteristic includes first and second edges of the chamber; and
determining the location of the chamber based on the first and second edges.

16. The method of claim 15, wherein the signal includes Raman scatter, and the structural characteristic is determined from the Raman scatter or fluorescence.

17. The method of claim 16, wherein the structural characteristic is determined from minimums in the Raman scatter.

18. The method of claim 17, further comprising:
employing the location to focus the second excitation signal at a sample in a reading region of the chamber.

19. The method of claim 18, wherein the location is determined prior to the sample being in the reading region.

20. The method of claim 18, wherein the sample includes a DNA sample being sequenced.

21. The method of claim 18, wherein the sample emits a signal in response to being illuminated by the second excitation signal, and further comprising:
detecting the signal emitted by the sample using a same detector used to detect the signal emitted by the sample carrier.

22. The method of claim 16, wherein the Raman scatter has a peak emission in a range about 570 nanometers.

23. The method of claim 22, wherein the excitation source has an emission spectrum in a range about 488 nanometers.

24. Computer readable instructions encoded on computer readable storage medium, which, when executed by a processor of a computing system causes the processor to:
identify a location of a chamber of a sample carrier based on a Raman scatter signal emitted from the sample carrier; and
employ the location of the chamber to direct an excitation signal at a sample in the chamber to process the sample.

* * * * *